United States Patent
Krafft et al.

(10) Patent No.: US 7,939,696 B2
(45) Date of Patent: May 10, 2011

(54) PROCESS FOR THE MANUFACTURE OF DICHLOROPROPANOL BY CHLORINATION OF GLYCEROL

(75) Inventors: Philippe Krafft, Rhode Saint Genese (BE); Christian Franck, Sterrebeek (BE); Ivan De Andolenko, Tavaux (FR); Roger Veyrac, Louvatange (FR)

(73) Assignee: Solvay Societe Anonyme, Brussels (BE)

( * ) Notice: Subject to any disclaimer, the term of this patent is extended or adjusted under 35 U.S.C. 154(b) by 0 days.

(21) Appl. No.: 12/092,178

(22) PCT Filed: Nov. 8, 2006

(86) PCT No.: PCT/EP2006/068208
§ 371 (c)(1),
(2), (4) Date: Apr. 30, 2008

(87) PCT Pub. No.: WO2007/054505
PCT Pub. Date: May 18, 2007

(65) Prior Publication Data
US 2008/0281132 A1    Nov. 13, 2008

Related U.S. Application Data

(60) Provisional application No. 60/734,637, filed on Nov. 8, 2005.

(51) Int. Cl.
*C07C 31/34* (2006.01)
(52) U.S. Cl. .................................................. 568/844
(58) Field of Classification Search ................. 568/839
See application file for complete search history.

(56) References Cited

U.S. PATENT DOCUMENTS

| | | |
|---|---|---|
| 865,727 A | 9/1907 | Queneau |
| 2,060,715 A | 11/1936 | Arvin |
| 2,063,891 A | 12/1936 | Dreyfus |
| 2,144,612 A * | 1/1939 | Heindel et al. ........... 568/844 |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A * | 11/1960 | Anderson et al. |
| 3,026,270 A | 3/1962 | Robinson, Jr. |
| 3,061,615 A | 10/1962 | Viriot et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,341,491 A | 9/1967 | Robinson et al. |
| 3,355,511 A | 11/1967 | Schwarzer |
| 3,385,908 A | 5/1968 | Schwarzer |
| 3,457,282 A | 7/1969 | Polak et al. |
| 3,711,388 A | 1/1973 | Gritzner |
| 3,839,169 A | 10/1974 | Moyer |
| 3,865,886 A | 2/1975 | Schindler et al. |
| 3,867,166 A * | 2/1975 | Sullivan |
| 3,954,581 A | 5/1976 | Carlin |
| 3,968,178 A | 7/1976 | Obrecht et al. |
| 4,011,251 A | 3/1977 | Tjurin et al. |
| 4,173,710 A | 11/1979 | Boulet et al. |
| 4,220,529 A | 9/1980 | Daude-Lagrave |
| 4,390,680 A | 6/1983 | Nelson |
| 4,405,465 A | 9/1983 | Moore et al. |
| 4,415,460 A | 11/1983 | Suciu et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Ishioka et al. |
| 4,655,879 A | 4/1987 | Brockmann et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,286,354 A | 2/1994 | Bard et al. |
| 5,344,945 A | 9/1994 | Grunchard |
| 5,359,094 A | 10/1994 | Teles et al. |
| 5,445,741 A | 8/1995 | Dilla et al. |
| 5,567,359 A | 10/1996 | Cassidy et al. |
| 5,578,740 A | 11/1996 | Au et al. |
| 5,710,350 A | 1/1998 | Jeromin et al. |
| 5,731,476 A | 3/1998 | Shawl et al. |

(Continued)

FOREIGN PATENT DOCUMENTS

CN    1296003 A    5/2001

(Continued)

OTHER PUBLICATIONS

Kirk-Othmer Encyclopedia of Chemical Technology, New York, Wiley, e-book, 2000-2010, vol. 13, p. 808-837.*

(Continued)

*Primary Examiner* — Brian J Davis
(74) *Attorney, Agent, or Firm* — Oblon, Spivak, McClelland, Maier & Neustadt, L.L.P.

(57) ABSTRACT

Process for the manufacture of dichloropropanol in which glycerol is reacted with a chlorinating agent comprising hydrochloric acid in a liquid medium in equilibrium with a vapor phase and in which the condensation of a fraction exhibiting the composition of the vapor phase is prevented.

14 Claims, No Drawings

U.S. PATENT DOCUMENTS

| | | | |
|---|---|---|---|
| 5,744,655 A | 4/1998 | Thomas et al. | |
| 5,779,915 A | 7/1998 | Becker et al. | |
| 5,908,946 A | 6/1999 | Stern et al. | |
| 5,993,974 A | 11/1999 | Fukushima et al. | |
| 6,142,458 A | 11/2000 | Howk | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,922 B1 | 2/2002 | Vosejpka et al. | |
| 6,740,633 B2 | 5/2004 | Norenberg et al. | |
| 7,126,032 B1 | 10/2006 | Aiken | |
| 7,128,890 B2 | 10/2006 | Ollivier | |
| 2001/0014763 A1 | 8/2001 | Ueoka et al. | |
| 2003/0209490 A1 | 11/2003 | Camp et al. | |
| 2004/0179987 A1 | 9/2004 | Oku et al. | |
| 2004/0232007 A1 | 11/2004 | Carson et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2007/0112224 A1 | 5/2007 | Krafft et al. | |
| 2008/0154050 A1 | 6/2008 | Gilbeau | |
| 2009/0022653 A1 | 1/2009 | Strebelle et al. | |
| 2009/0198041 A1 | 8/2009 | Krafft et al. | |
| 2009/0270588 A1 | 10/2009 | Krafft et al. | |
| 2009/0275726 A1 | 11/2009 | Krafft et al. | |

FOREIGN PATENT DOCUMENTS

| | | | |
|---|---|---|---|
| DE | 58396 | | 8/1891 |
| DE | 180 668 | | 11/1906 |
| DE | 197308 C | | 11/1906 |
| DE | 238341 C | | 3/1908 |
| DE | 197309 C | | 4/1908 |
| DE | 1 041 488 | | 10/1958 |
| DE | 1 075 103 | | 2/1960 |
| DE | 1 226 554 | | 10/1966 |
| DE | 30 03 819 | | 8/1981 |
| DE | 216 471 | | 6/1983 |
| DE | 3243617 | | 5/1984 |
| DE | 3 721 003 | | 6/1987 |
| DE | 102 03 914 | | 1/2002 |
| DE | 102 54 709 | | 6/2004 |
| DE | 238341 | | 3/2008 |
| EP | 0 296 341 | | 12/1988 |
| EP | 0 347 618 | | 12/1989 |
| EP | 0 421 379 | | 4/1991 |
| EP | 0518765 A | | 12/1992 |
| EP | 0 522 382 | | 1/1993 |
| EP | 0 535 949 | | 4/1993 |
| EP | 0 563 720 | | 10/1993 |
| EP | 0 568 389 | | 11/1993 |
| EP | 0 582 201 | | 2/1994 |
| EP | 0 916 624 | | 5/1999 |
| EP | 0 919 551 | | 6/1999 |
| EP | 1 059 278 | | 12/2000 |
| EP | 1 106 237 | | 6/2001 |
| EP | 1 153 887 | | 11/2001 |
| EP | 1 163 946 | | 12/2001 |
| EP | 1 298 154 | | 4/2003 |
| EP | 0 561 441 | | 9/2003 |
| EP | 1 411 027 | | 4/2004 |
| EP | 1 752 435 A1 | | 2/2007 |
| EP | 1 752 436 A1 | | 2/2007 |
| EP | 1 760 060 A1 | | 3/2007 |
| EP | 1 762 556 | | 3/2007 |
| EP | 1 770 081 A1 | | 4/2007 |
| EP | 1 772 446 A1 | | 4/2007 |
| EP | 1 775 278 A1 | | 4/2007 |
| EP | 2 085 364 | | 8/2009 |
| FR | 1 476 073 | | 4/1966 |
| FR | 2 180 138 | | 5/1973 |
| FR | 2 565 229 | | 12/1985 |
| FR | 2 752 242 | | 2/1998 |
| FR | 2 862 644 | | 5/2005 |
| FR | 2 868 419 | | 10/2005 |
| FR | 2 869 612 | | 11/2005 |
| FR | 2 869 613 | | 11/2005 |
| FR | 2872504 A | | 1/2006 |
| FR | 2881732 A | | 8/2006 |
| FR | 2 885 903 | | 11/2006 |
| FR | 2 912 743 | | 8/2008 |
| FR | 2 913 683 | | 9/2008 |
| FR | 2913683 A1 * | | 9/2008 |
| FR | 2 918 058 | | 1/2009 |
| FR | 2 925 045 | | 6/2009 |
| FR | 2 929 611 | | 10/2009 |
| FR | 2 935 699 | | 3/2010 |
| FR | 2 935 968 | | 3/2010 |
| GB | 14767 A | | 0/1914 |
| GB | 404 938 | | 7/1932 |
| GB | 406345 | | 8/1932 |
| GB | 467 481 | | 9/1935 |
| GB | 541357 A * | | 11/1941 |
| GB | 702143 | | 10/1950 |
| GB | 679536 A | | 9/1952 |
| GB | 736641 | | 7/1953 |
| GB | 799567 A | | 8/1958 |
| GB | 1083594 | | 11/1964 |
| GB | 984446 A * | | 2/1965 |
| GB | 984633 A | | 3/1965 |
| GB | 1 387 668 | | 3/1972 |
| GB | 1286893 A * | | 8/1972 |
| GB | 1414976 A | | 11/1975 |
| GB | 2 173 496 | | 10/1986 |
| GB | 2 336 584 | | 10/1999 |
| JP | 39-27230 | | 11/1939 |
| JP | 55-041858 | | 3/1980 |
| JP | 56-29572 | | 3/1981 |
| JP | 56-99432 | | 8/1981 |
| JP | 61-112066 | | 5/1986 |
| JP | 62-242638 | | 10/1987 |
| JP | 63-195288 | | 8/1988 |
| JP | 03-014527 | | 1/1991 |
| JP | 03-223267 | | 10/1991 |
| JP | 3-223267 | | 10/1991 |
| JP | 04-089440 | | 3/1992 |
| JP | 04-217637 | | 8/1992 |
| JP | 6-25196 | | 4/1994 |
| JP | 6-184024 | | 7/1994 |
| JP | 06-321852 | | 11/1994 |
| JP | 8-59593 | | 3/1996 |
| JP | 09-299953 | | 11/1997 |
| JP | 10-139700 | | 5/1998 |
| JP | 10-218810 | | 8/1998 |
| JP | 2001-213827 | | 8/2001 |
| JP | 2001-1261581 | | 9/2001 |
| JP | 2002-02033 | | 1/2002 |
| JP | 2002-038195 | | 2/2002 |
| JP | 2002-363153 | | 12/2002 |
| JP | 2003 081891 | | 3/2003 |
| JP | 2003-89680 | | 3/2003 |
| JP | 2005-007841 | | 1/2005 |
| JP | 2005-097177 | | 4/2005 |
| JP | 76021635 | | 4/2005 |
| KR | 2003-29740 | | 5/2003 |
| KR | 10-0514819 | | 11/2004 |
| SU | 123153 | | 1/1959 |
| SU | 1125226 | | 11/1984 |
| SU | 1159716 | | 6/1985 |
| SU | 1685969 | | 10/1991 |
| WO | WO 96/07617 | | 3/1996 |
| WO | WO 97/48667 | | 12/1997 |
| WO | WO 98/37024 | | 8/1998 |
| WO | WO 99/32397 | | 7/1999 |
| WO | WO 01/86220 | | 11/2001 |
| WO | WO 02/26672 | | 4/2002 |
| WO | WO 03/064357 | | 8/2003 |
| WO | WO 2007/144335 | | 12/2003 |
| WO | WO 2005/021476 | | 3/2005 |
| WO | WO 2005/054167 | | 6/2005 |
| WO | WO 2005/097722 | | 10/2005 |
| WO | WO 2005/115954 | | 12/2005 |
| WO | WO 2005/116004 | | 12/2005 |
| WO | WO 2006/020234 | | 2/2006 |
| WO | WO 2006/100311 | | 9/2006 |
| WO | WO 2006/100311 A2 | | 9/2006 |
| WO | WO 2006/100312 A2 | | 9/2006 |

| | | |
|---|---|---|
| WO | WO 2006/100313 A2 | 9/2006 |
| WO | WO 2006/100314 A1 | 9/2006 |
| WO | WO 2006/100315 A1 | 9/2006 |
| WO | WO 2006/100315 A2 | 9/2006 |
| WO | WO 2006/100316 A1 | 9/2006 |
| WO | WO 2006/100317 A1 | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 | 5/2007 |
| WO | WO 2007/054505 A2 | 5/2007 |
| WO | WO 2007/144335 A1 * | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

Chemistry of the Elements, Greenwood et al., Pergamon Press Ltd, London, 1984, p. 949-951.*
Derwent Publications, AN 109:6092 CA, JP 62-242638, Oct. 23, 1987.
Derwent Publications, AN 1987-338139 [48], JP 62-242638, Oct. 23, 1987.
Herman A. Bruson, et al., "Thermal Decomposition of Glyceryl Carbonates," Journal of the American Chemical Society, vol. 74, Apr. 1952 pp. 2100-2101.
J.B. Conant et al., "Glycerol α,γ-dichlorophydrin", Organic Sytheses Coll., 1941, vol. 1, p. 292-294 (5 pp.).
K. Weissermel and H-J. Arpe in Industrial Organic Chemistry, Third, Completely Revised Edition, VCH, 1997. pp. 149,275.
Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition. 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429.
Ullmann's Encyclopedia of Industrial Chemistry, Fifth Completely Revised Edition, vol. A6, pp. 240-252.
Hancock, E.G., Propylene and Its Industrial Derivatives, 1973, pp. 298-332.
K. Weissermel and H. J. Arpe in Industrial Organic Chemistry, Third, Completely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H, Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.
Semendyava, ND et al. 1981, Kimicheskaya Promyshlennost. Seriya: Khornaya Promysshlennost. 5. 21-2 (CA Summary), XP 002465275.
Rudenenko, EV, et al., 1988 Kakokrasochnye Materialy 1 kh Primenenic, 4. 69-71 (CA Summary). XP 002465276.
Kirk-Othmer Encyclopedia of Chemical Technology, 1978, $3^{rd}$ Ed., vol. 4, Blood, Coagulants and Anticoagulants to Cardiovascular Agents. p. 847-848.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
I. Miyakawa et al., Nagoya Sangyo Kagaku Kenkyusho Kenkyu Hokoku, 10, 49-52 (1957). (Abstract in English only).
Han Xiu-Ying et al., Shanxi Daxue Xueba Blanjibu, 2002, 25(4), 379-80). (Abstract in English only).
Gibson, "The preparation, properties, and uses of glycerol, derivatives, Part III. The Chlorohydrins", 1931, Chemistry and Industry, Chemical Society, pp. 949-975.
Carre et al., 1931, "La transformation des alcools polyatomiques en mono- et en polychlorohydrines au moyen du chlorure de thionyle", Bulletin De Le Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, $5^{th}$ Ed., vol. A9, pp. 539-540.
Bonner et al., "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, $5^{th}$ Ed., vol. A9, pp. 547-563.
Novelli, A., "The preparation of mono- and dichlorohydrins of glycerol", 1930, Anales Farmacia Bioquimica, vol. 1, pp. 8-19 (with English abstract).
Perry's Chemical Engineers Handbook $7^{th}$ Ed., $11^{th}$ Section, 1997, pp. 11.1-11.118.*
Perry's Chemical Engineers Handbook $7^{th}$ Ed., $13^{th}$ Section, 1997, pp. 13.1-13.108.*
Perry's Chemical Engineers Handbook $7^{th}$ Ed., $15^{th}$ Section, 1997, pp. 15.1-15.47.*
Ullmann's Encyclopedia of Industrial Chemistry $5^{th}$ Ed., vol. A23, 1993, pp. 635-636.*
Ullmann's Encyclopedia of Industrial Chemistry $5^{th}$ Ed., vol. A13, 1989, pp. 289.*
Ullmann's Encyclopedia of Industrial Chemistry $5^{th}$ Ed., vol. A11, 1988, pp. 354-360.*
Attached certified copy of Application No. FR 06.05325 filed Jun. 14, 2006 by Solvay SA—priority document to EP2007/55742 published as WO2007/144335 (attached herein).*
Attached certified copy of Application No. FR 07.53863 filed Mar. 15, 2007 by Solvay SA and published as FR2913683 (attached herein)—priority document to EP2007/55742 published as WO2007/144335 (attached herein).*
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide. Chemical Daily Co., Ltd. (Published on Jun. 15, 1990) with attached English translation of relevant excerpts.
Robert T. Morrison & Robert N. Boyd Organic Chemistry, vol. II, pp. 666 to 667 and 712 to 714 (Japanese Translation), published on Jul. 10, 1970, Tokyo Kagaku Dozin Co.. Ltd. (and similar passages but retrieved from the English Fifth Edition of the Book, 1987).

U.S. Appl. No. 11/914,879, filed Nov. 19, 2007, Gilbeau.
U.S. Appl. No. 11/915,059, filed Nov. 20, 2007, Gilbeau, et al.
U.S. Appl. No. 11/914,836, filed Nov. 19, 2007, Krafft, et al.
U.S. Appl. No. 60/734,659, filed Nov. 8, 2005.
U.S. Appl. No. 11/915,067, filed Nov. 20, 2007, Krafft, et al.
U.S. Appl. No. 60/734,627, filed Nov. 8, 2005.
U.S. Appl. No. 11/914,874, filed Nov. 19, 2007, Krafft, et al.
U.S. Appl. No. 60/734,657, filed Nov. 8, 2005.
U.S. Appl. No. 11/914,862, filed Nov. 19, 2007, Gilbeau.
U.S. Appl. No. 60/734,658, filed Nov. 8, 2005.
U.S. Appl. No. 11/914,856, filed Nov. 19, 2007, Krafft, et al.
U.S. Appl. No. 60/734,635, filed Nov. 8, 2005.
U.S. Appl. No. 11/914,868, filed Nov. 19, 2007, Krafft.
U.S. Appl. No. 60/734,634, filed Nov. 8, 2005.
U.S. Appl. No. 11/915,046, filed Nov. 20, 2007, Krafft, et al.
U.S. Appl. No. 60/734,636, filed Nov. 8, 2005.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
Medium and Long-Term Opportunities and Risks of the Biotechnologial Production of Bulk Chemicals from Renewable Resources—The Potential of White Biotechnology—The Brew Project—Final Report—Prepared under the European Commission's GRXTH Programme (DG Research) Utrecht, Sep. 2006 (pp. 29-31).
Ullmann Encyl. Industr. Chem., $5_{th}$ Ed., vol. A6, (1988), pp. 401-477.
Polymer Science Dictionary, M.S.M., Elsevier Applied Chemistry, London and New York 1989, p. 86.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V; - 2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997, p. 347-355.
Ying Ling Liu, "Epoxy Resins from Novel Monomers with a Bis-(9,10-dihydro-9-oxa-10-oxide-0-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).

M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/English Abstract.
U.S. Appl. No. 12/529,777, filed Sep. 3, 2009, Krafft, et al.
U.S. Appl. No. 12/527,538, filed Aug. 17, 2009, Gilbeau, et.
U.S. Appl. No. 12/600,018, filed Nov. 13, 2009, Borremans.
U.S. Appl. No. 12/529,778, filed Sep. 3, 2009, Krafft, et al.
U.S. Appl. No. 12/663,749, filed Dec. 9, 2009, Krafft, et al.
U.S. Appl. No. 12/663,753, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
U.S. Appl. No. 60/734,637, filed Nov. 8, 2005, Krafft et al.
U.S. Appl. No. 12/527,538, filed Aug. 17, 2009, Gilbeau, et al.
U.S. Appl. No. 12/600,018, filed Nov. 13, 2009, Borremans, et al.
U.S. Appl. No. 12/681,083, filed Mar. 31, 2010, Bobet, et al.
Ullmann's Encyclopedia of Industrial Chemistry, 2005, Wiley-VCH GmbH & Co., KgaA, Weinhem, pp. 8-15 and 401-477, Published online Mar. 15, 2001.
RD 436093, Aug. 10, 2000, Research Disclosure.
U.S. Appl. No. 12/864,211, filed Jul. 27, 2010, Gilbeau, et al.
U.S. Appl. No. 12/745,802, filed Jun. 2, 2010, Gilbeau, et al.
"Epoxy resins", p. 36-46, by Shangai Resin Plant, Shangai Peoples's Press, 1971—attached English translation only.
Martinetti, R. et al. "Environnement Le Recyclage de l'eau" Industrie Textile, Ste Sippe Sarl, Metz, FR, n° 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/Ietc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Microchemical Journal, vol. 85, N°2, pp. 183-193; available online Aug. 17, 2006; 12 pp.
Oleoline, com, Glycerine Market report, Sep. 10, 2003, No. 62.
Notification Under Act. No. 100/2001, Coll. As Amended by Act No. 93/2004, Coll. To the extent of Annex No. 4, (SPOLEK) Nov. 30, 2004.
Documentation Under Act. No. 100/2001 Coll. As amended by Act No. 93/2004 Coll in the scope of appendix No. 4 (SPOLEK) Jan. 11, 2005.
Ma Zengxin, Gan Yicui, Recovery of Polyglycerol from Residues of Synthetic Glycerol—Riyong Huaxue Gongye, 1997, 4, 21023 (Abstract Only).
U.S. Appl. No. 12/935,538, filed Sep. 29, 2010, Gilbeau, et al.

* cited by examiner

PROCESS FOR THE MANUFACTURE OF DICHLOROPROPANOL BY CHLORINATION OF GLYCEROL

CROSS-REFERENCE TO RELATED APPLICATIONS

This application claims priority to U.S. Application No. 60/734,637, filed Nov. 8, 2005, the entirety of which is incorporated herein by reference.

The present patent application claims the benefit of provisional U.S. patent application 60/734637 filed on 8 Nov. 2005, the content of which is incorporated herein by reference.

The present invention relates to a process for the manufacture of dichloropropanol in which glycerol and a chlorinating agent are reacted optionally in the presence of an organic acid, so as to obtain reaction products comprising dichloropropanol. The dichloropropanol can be separated from the other reaction products and can be subjected to a dehydrochlorination reaction, so as to manufacture epichlorohydrin. Such a process is disclosed in Application WO 2005/054167 of SOLVAY SA, the content of which is incorporated in the present application by reference. A preferred chlorinating agent is hydrogen chloride.

In this process, the reaction between glycerol and the chlorinating agent is preferably carried out in a reactor and related ancillary equipments made of or coated with materials resistant to chlorinating agents and in particular to hydrogen chloride under the reaction conditions. Enamelled (glass-lined) steel is a preferred vessel material. The applicant has found that such materials remain however unsatisfactory, i.e. they are corroded by liquid mixtures containing water, dichloropropanol and hydrogen chloride, resulting from the condensation of rich hydrogen chloride content vapours on the inner walls of the reactor and of related ancillary equipments.

This aim of this invention is to provide a process for manufacturing dichloropropanol which does not exhibit that problem.

The invention therefore relates to a process for the manufacture of dichloropropanol in which glycerol is reacted with a chlorinating agent comprising hydrogen chloride, wherein, in a vessel, a liquid medium is in equilibrium with a vapour phase and wherein at least one part of the inner wall of the vessel which is above the level of the liquid medium in the vessel is maintained at a temperature lower than 120° C. or at a temperature at least 1° C. higher than the dew temperature of the vapour phase and/or is trickled with a liquid.

The part of the inner wall of the vessel which is above the level of the liquid medium in the vessel is maintained at the required temperature continuously or intermittently.

The temperature of 120° C. is the temperature at which corrosion of enamelled steel at a rate of at least 0.01 mm/year is observed in the presence of hydrogen chloride/water liquid mixtures containing at least 4% by weight of hydrogen chloride.

The vessel can be any vessel of the process for manufacturing the dichloropropanol where the temperature of the liquid phase is higher than 120° C., like for instance a reactor, a distillation column, a stripping column or a decanter.

It has now been found that by working under such conditions of temperature and/or wetting conditions the corrosion of the inner vessel wall above the level of the liquid medium can be reduced. Without wishing to be bound by any theory, it is believed that when the temperature of the inner wall of the vessel which is above the level of the liquid medium in the vessel is lower than 120° C., the corrosion rate is reduced even in contact with very corrosive condensed mixtures containing water, hydrogen chloride and dichloropropanol. It is also believed that when the temperature of the inner wall of the vessel which is above the level of the liquid medium in the vessel is at a temperature at least 1° C. higher than the dew temperature of the vapour phase above the liquid medium, the corrosion rate is reduced due to a reduced condensation of vapours containing water, hydrogen chloride and dichloropropanol. Finally, it is also believed that when the inner wall of the vessel which is above the level of the liquid medium in the vessel is trickled with a liquid, the corrosiveness of condensed mixtures containing water, hydrogen chloride and dichloropropanol is reduced by dilution. The reduction of the corrosion of the constituent materials of the vessel makes it possible to further limit the costs associated with the replacement of the latter.

In the liquid corrosive mixtures obtained by condensation of the vapours containing water, hydrogen chloride and dichloropropanol, the hydrogen chloride content is generally higher than or equal to 1% by weight of the mixture, frequently higher than or equal to 3% and often greater than or equal to 5%. The hydrogen chloride content is generally lower than or equal to 80% by weight of the mixture, frequently lower than or equal to 60% and often lower than or equal to 50%.

In the liquid corrosive mixtures obtained by condensation of the vapours containing water, hydrogen chloride and dichloropropanol, the water content is generally higher than or equal to 4% by weight of the mixture, frequently higher than or equal to 5% and often greater than or equal to 10%. The water content is generally lower than or equal to 80% by weight of the mixture, frequently lower than or equal to 70% and often lower than or equal to 60%.

In the liquid corrosive mixtures obtained by condensation of the vapours containing water, hydrogen chloride and dichloropropanol, the dichloropropanol content is generally higher than or equal to 4% by weight of the mixture, frequently higher than or equal to 5% and often greater than or equal to 10%. The dichloropropanol content is generally lower than or equal to 80% by weight of the mixture, frequently lower than or equal to 70% and often lower than or equal to 60%.

Others compounds can also be present in the liquid corrosive mixtures containing water, hydrogen chloride and dichloropropanol, like for instance glycerol, monochloropropanediol, and esters thereof.

The level of the liquid medium in the vessel is defined as the level of the liquid when the vessel is operating in stationary regime.

The inner wall of the vessel which is above the level of the liquid medium in the vessel generally extends above the level of the liquid medium in the vessel to the top of the vessel.

According to a first embodiment of the process of the invention, the temperature of the inner wall of the vessel which is above the level of the liquid medium in the vessel is at a temperature lower than 120° C., preferably lower than or equal to 110° C., more preferably lower than or equal to 100° C. and most preferably lower than or equal to 90° C.

According to a first variant of the first embodiment, the internal wall of the vessel which is above the level of the liquid medium in the vessel is cooled down by means of an external cooling system. That system can be for instance a cooling fluid circulating between the inner and outer wall of the part of the vessel (double-walled conventional jacket) which is above the level of the liquid medium in the vessel or a cooling fluid circulating in a serpentine welded on the vessel wall or connected by a thermally conductive cement or located within the protective layer (for instance serpentine flooded in the protective layer or channel drilled in the bulk of the protective layer) or a semi-shell tube (half-pipe jacket) in contact with the outer wall of the vessel which is above the level of the liquid medium in the vessel or by flushing a cooling fluid on the outer wall of the vessel which is above the level of the liquid medium in the vessel. The cooling fluid can be a gas or a liquid. It is preferred to use a gaseous fluid when flushing the outer wall. The gas can be for example dry air or nitrogen. It is preferred to use a liquid fluid when circulating in double-walled envelope and serpentines. The liquid can be an organic liquid, an inorganic liquid or a mixture thereof. It is preferred to use an inorganic liquid, more preferably water.

According to a second variant of the first embodiment, the inner wall of the vessel which is above the level of the liquid medium in the vessel is cooled down by flushing a cooling fluid on the inner wall. The fluid can be a gas or a liquid. The gas can for instance be hydrogen chloride or steam. The temperature of the gas is lower than the temperature of the liquid medium. The fluid is preferably a liquid. The liquid can be selected from a cold condensate arising from the treatment of the vapour phase in equilibrium with the liquid medium in a distillation, evaporation or stripping column, or selected from glycerol, water, an aqueous solution of hydrogen chloride, dichloropropanol, monochloropropanediol and mixtures thereof. By cold condensate, one intends to denote a condensate which temperature is lower than the temperature of the vapour phase in equilibrium with the liquid medium.

The temperature of the cooling fluid is adjusted to obtain the inner wall temperature mentioned above.

According to a second embodiment of the process of the invention, the temperature of the inner wall of the vessel which is above the level of the liquid medium in the vessel is at a temperature at least 1° C. higher than the dew temperature of the vapour above the liquid medium, preferably at least 3° C. higher, more preferably at least 5° C. higher and most preferably at least 10° C. higher.

According to a first variant of that second embodiment, the inner wall of the vessel which is above the level of the liquid medium in the vessel is heated up by means of an external heating system. That system can be for instance a heating fluid circulating between the inner and outer wall (double-walled conventional jacket) of the part of the vessel which is above the level of the liquid medium in the vessel or a heating fluid circulating in a serpentine welded to the vessel wall or connected by a thermally conductive cement or in a semi-shell tube (half-pipe jacket) in contact with the outer wall of the vessel which is above the level of the liquid medium in the vessel or by flushing a heating fluid on the outer wall of the vessel which is above the level of the liquid medium in the vessel. The heating of the part of the vessel which is above the level of the liquid medium in the vessel can also be carried out by using electric tracing or by radiation, such as electromagnetic radiations like for instance Infra Red radiations. When a heating fluid is used, it can be a gas or a liquid. When a double-walled envelope or a serpentine or a semi-shell system is used for the external heating, it is preferred to use a liquid. The liquid can be an organic, an inorganic liquid or a mixture thereof. An inorganic liquid is preferred, pressurized water being most preferred. When the heating is carried out by flushing a heating fluid, the fluid is preferably a hot gas. By hot gas, one intends to denote a gas with a temperature is higher than the temperature of the liquid medium. The gas can be nitrogen, air or steam. Steam is more preferred. Steam with a pressure lower than 10 absolute bar is the most preferred.

According to a second variant of that second embodiment, the internal wall of the vessel which is above the level of the liquid medium in the vessel is heated up by means of an internal heating system and a thermally insulating device can optionally be placed on the external wall of the vessel which is above the level of the liquid medium. The internal heating is carried out by flushing a heating fluid on the inner wall. By heating fluid, one intends to denote a fluid with a temperature higher than the temperature of the liquid medium. The fluid can for instance be nitrogen, steam, hydrogen chloride or low boiling compounds produced by the reaction between glycerol and hydrogen chloride like for instance dichloropropanol, or mixture thereof. The gas can be introduced in the vessel by any suitable way, like for instance above the level of the liquid medium in the vessel in such a way that a helicoidal stream of gas is produced above that level.

The temperature of the heating fluid is adjusted to obtain the inner wall temperature mentioned above.

Any kind of thermally insulating device can be used. Insulating material can be made of inorganic material like perlite, of organic material or mixture thereof.

According to a third embodiment of the process of the invention, the inner wall of the vessel which is above the level of the liquid medium in the vessel is trickled with a liquid. The liquid can be selected from a cold condensate arising from the treatment of the vapour phase in equilibrium with the liquid medium in a distillation, evaporation or stripping column, or selected from glycerol, water, an aqueous solution of hydrogen chloride, dichloropropanol and monochloropropanediol, and mixtures thereof. By cold condensate, one intends to denote a condensate which temperature is lower than the temperature of the vapour phase in equilibrium with the liquid medium. The liquid can be selected from another part of the process with a low concentration of hydrogen chloride.

The various embodiments which have been described above can be combined.

According to a fourth embodiment of the process of the invention, the inner wall of the vessel which is above the level of the liquid medium in the vessel, can be heated and trickled with a liquid. In that embodiment, it is preferred to heat the upper part of the inner wall and to trickle the lower of the inner wall which is above the level of the liquid medium in the vessel. The lower part generally extends from the level of the liquid medium in the vessel to 0.1 m above that level, The upper part generally extends from 0.5 m above the level of the liquid medium to the top of the vessel.

According to a fifth embodiment of the process of the invention, the inner wall of the vessel which is above the level of the liquid medium in the vessel, can be cooled and trickled with a liquid.

The examples below are intended to illustrate the invention without, however, imposing any limitation thereon.

EXAMPLE 1

Not According to the Invention

When contacted with a water-hydrogen chloride liquid mixture containing 20% by weight of hydrogen chloride at 120° C., an enamelled-lined steel sample exhibits a corrosion rate of 0.035 mm/year.

EXAMPLE 2

According to the Invention

When contacted with a water-hydrogen chloride liquid mixture containing 20% by weight of hydrogen chloride at 50° C., an enamelled-lined steel sample exhibits a corrosion rate of less than 0.010 mm/year.

The invention claimed is:

1. A process for the manufacture of dichloropropanol in which glycerol is reacted with a chlorinating agent comprising hydrogen chloride in a vessel in which a liquid medium is in equilibrium with a vapour phase and according to which corrosion of at least a part of an inner vessel wall above the level of the liquid medium is at least partially avoided by:
  (i) heating said inner vessel wall in order to maintain at least part of the inner vessel wall at a temperature at least 1° C. higher than the dew temperature of the vapour phase, or
  (ii) trickling said inner vessel wall with a liquid having a temperature which is lower than the temperature of the vapor phase, or
  (iii) trickling said inner vessel wall with a liquid having a composition that allows to dilute a condensed vapor phase, or
  (iv) combining (ii) and (v) where (v) is:
  (v) cooling said inner vessel wall in order to maintain at least part of the inner vessel wall at a temperature lower than 120° C.,
  or combining (iii) and (v),
  or combining (ii) and (iii) and (v),
  or combining (i) and (iii).

2. The process according to claim 1 comprising (i) wherein the internal wall of the vessel which is above the level of the liquid medium in the vessel is maintained at a temperature at least 1° C. higher than the dew temperature of the vapour phase by heating by:
  (A) an external heating system selected from a heating fluid circulating in a serpentine or a semi-shell tube in contact with the outer wall of the vessel or by flushing a heating fluid on the outer wall of the vessel which is above the level of the liquid medium in the vessel or
  (B) an internal heating system which consists of flushing a heating fluid on the inner wall of the vessel which is above the level of the liquid medium in the vessel or
  (C) both (A) and (B).

3. The process according to claim 2 wherein an internal heating system is used and a thermally insulating device is placed on the external wall of the vessel which is above the level of the liquid medium.

4. The process according to claim 1 comprising (ii) or (iii) wherein the inner wall of the vessel which is above the level of the liquid medium in the vessel is trickled with a liquid selected from a cold condensate arising from the treatment of the vapour phase in equilibrium with the liquid medium in a distillation, evaporation or stripping column, or selected from glycerol, water, an aqueous solution of hydrogen chloride, dichloropropanol, monochloropropanediol and mixtures thereof.

5. The process according to claim 1, comprising (i).

6. The process according to claim 1, comprising (ii).

7. The process according to claim 1, comprising (iii).

8. The process according to claim 1, comprising (ii) and (v).

9. The process according to claim 1, comprising (iii) and (v).

10. The process according to claim 1, comprising (ii) and (iii) and (v).

11. The process according to claim 1, comprising (i) and (iii).

12. The process according to claim 2, comprising (A).

13. The process according to claim 2, comprising (B).

14. The process according to claim 2, comprising (C).

* * * * *

UNITED STATES PATENT AND TRADEMARK OFFICE
CERTIFICATE OF CORRECTION

| | | |
|---|---|---|
| PATENT NO. | : 7,939,696 B2 | Page 1 of 1 |
| APPLICATION NO. | : 12/092178 | |
| DATED | : May 10, 2011 | |
| INVENTOR(S) | : Philippe Krafft et al. | |

It is certified that error appears in the above-identified patent and that said Letters Patent is hereby corrected as shown below:

Column 5, line 7, "vapour" should read --vapor--;
　　　　　line 12, "vapour" should read --vapor--;
　　　　　line 30, "vapour" should read --vapor--.
Column 6, line 15, "vapour" should read --vapor--.

Signed and Sealed this
Nineteenth Day of July, 2011

David J. Kappos
*Director of the United States Patent and Trademark Office*